(12) United States Patent
Brunke

(10) Patent No.: US 8,727,995 B2
(45) Date of Patent: May 20, 2014

(54) REDUCTION OF MOTION ARTIFACTS IN ULTRASOUND IMAGING WITH A FLEXIBLE ULTRASOUND TRANSDUCER

(75) Inventor: Shelby Brunke, Sammamish, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 540 days.

(21) Appl. No.: 12/878,798

(22) Filed: Sep. 9, 2010

(65) Prior Publication Data

US 2012/0065507 A1 Mar. 15, 2012

(51) Int. Cl.
*A61B 8/14* (2006.01)

(52) U.S. Cl.
USPC .......................................... 600/466; 600/462

(58) Field of Classification Search
USPC .......................................... 600/437–438, 462
See application file for complete search history.

(56) References Cited

U.S. PATENT DOCUMENTS

| 2009/0149753 | A1* | 6/2009 | Govari et al. | 600/439 |
| 2010/0286516 | A1* | 11/2010 | Fan et al. | 600/438 |
| 2010/0286520 | A1* | 11/2010 | Hazard et al. | 600/439 |

OTHER PUBLICATIONS

Urban et al., "Modulation of ultrasound to produce mutlifrequency radiation force", Mar. 2010, Acoustical Society of America, pp. 1228-1238.*
Hsu et al., "Novel Acoustic Radiation Force Impulse Imaging Methods for Visualization of Rapidly Moving Tissue", Jul. 2009.*
U.S. Appl. No. 12/240,044, filed Sep. 29, 2008.
Stephen J. Hsu, et al., "Challenges and Implementation of Radiation-Force Imaging with an Intracardiac Ultrasound Transducer", IEEE Transactions on Ultrasonics, Ferroelectrics, and Frequency Control, vol. 54, No. 5, May 2007, pp. 996-1009.

* cited by examiner

*Primary Examiner* — Christopher Cook

(57) ABSTRACT

Reduction of motion artifacts from flexible transducers are provided in ultrasound imaging. Temporal and/or amplitude modulation of an acoustic radiation force impulse pushing pulse may be designed to control the motion of a moveable transducer. The motion may be controlled to stabilize the transducer in one position or in a predictable (e.g. linear) movement in order to better estimate tissue displacement. Reduced motion artifact may be provided with transmitted waveforms requiring less time and power than required of a brute force approach. For example, pre-loading transmissions may not be provided. As another example, pre-loading transmissions may require less than 10 ms.

9 Claims, 4 Drawing Sheets

REDUCTION OF MOTION ARTIFACTS IN ULTRASOUND IMAGING WITH A FLEXIBLE ULTRASOUND TRANSDUCER

BACKGROUND

The present embodiments relate to motion artifacts in ultrasound imaging. Ultrasound transducers may recoil due to transmission of acoustic energy, causing a motion artifact.

Recoil may occur in any mode of ultrasound imaging. Shear wave and elasticity imaging modes may be more susceptible to motion artifact from recoil in modes such as acoustic radiation force impulse (ARFI) imaging due to the greater acoustic energy used in push pulses. ARFI provides the ability to assess the stiffness of tissue, both in a relative and absolute sense. ARFI imaging exploits the fact that a portion of the acoustic energy transmitted into the tissue is converted into a radiation force that acts on the tissue in the direction of the acoustic beam. This force is proportional to the attenuation and the spatially averaged intensity of the acoustic pulse. The stiffness properties of the tissue can be ascertained by interrogating the induced tissue displacements in the longitudinal or transverse (shear) directions.

ARFI imaging may be performed with a transducer array mounted on a catheter, such as a cardiac catheter. One consequence of ARFI imaging that impacts flexible intra-cardiac echo (ICE) devices is that a long high intensity acoustic pulse transmitted from the catheter generates a reactionary force or recoil. The recoil may generate appreciable displacement in the transducer itself. Hsu, et al., "Challenges and Implementation of Radiation Force Imaging with an Intracardiac Ultrasound Transducer," IEEE UFFC, Vol. 54, no. 5, May, 2007, have demonstrated that the motion in an ICE device peaks at about 8 um after 5 msec (see FIG. 1a, reproduced from the Hsu article). The average maximum longitudinal tissue displacements that are observed in ARFI imaging are on the order of 2-6 um, as shown in Table 1, reproduced from the Hsu article.

TABLE 1

PRE- AND POSTABLATION AVERAGE MAXIMUM DISPLACEMENTS.

| | Average maximum displacement (μm) | | |
|---|---|---|---|
| | Left | Center | Right[1] |
| Preablation | 2.63 ± 0.33 | 5.60 ± 1.10 | 4.72 ± 1.52 |
| Mid-ablation | 2.59 ± 0.32 | 4.91 ± 0.67 | 3.45 ± 0.78 |
| Postablation | 2.70 ± 0.25 | 5.31 ± 1.13 | 2.46 ± 0.44 |

The motion of the transducer (e.g., 8 um) may completely confound the estimation of the ARFI induced tissue displacements (e.g., average 2-6 um).

To address this problem, Hsu, et al. take a brute force approach. A long series of acoustic pulses are transmitted to push the transducer head back to a pre-loaded position before beginning ARFI imaging. The imaging pulses that are fired to create a 2D ARFI image then cause a roughly linear increase in displacement with each repetition of a pushing or ARFI pulse. FIG. 1b, reproduced from the Hsu article, shows about 25 ms worth of preloaded transmissions to place the transducer in a position to respond to ARFI with linear offset. The preloading transitions the transducer through nonlinear movement and into a linear movement region starting at about 30 ms. However, the ability to transmit such long preloading pulses may be limited by heating and power considerations.

BRIEF SUMMARY

By way of introduction, the preferred embodiments described below include methods, instructions, and systems for reduction of motion artifacts in ultrasound imaging. Temporal and/or amplitude modulation of the ARFI pushing pulse may be designed to control motion of a moveable transducer. The pushing pulse sequence may be designed and controlled, in combination with a dynamic model of the transducer, to achieve a desired dynamic response of the transducer. The desired dynamic response is most likely to be a minimization of the transducer motion or a predictable transducer motion response that can be easily accounted for when processing the received echoes. By considering the transducer to be a flexible structure and the acoustic imaging and push pulses to be a force input to that flexible structure, pulses may be designed to achieve the required acoustic insonification for the imaging mode while minimizing motion artifacts. The duration between pulses, duration of pulses, and/or amplitude vary in the sequence to achieve desired transducer response. The model may be designed to produce transmitted waveforms requiring less time and power to achieve ARFI imaging than transmitting a same pulse over and over. For example, pre-loading transmissions may not be provided. As another example, pre-loading transmissions may require less than 10 ms.

In a first aspect, a system is provided for reduction of motion artifacts in ultrasound imaging. A catheter includes an ultrasound transducer and a flexible portion. A transmit beamformer is operable to generate an acoustic radiation force pushing pulse having a maximum amplitude and lasting for a first duration. The acoustic radiation force pushing pulse is modulated in amplitude. The modulation includes variation such that transmission of the acoustic radiation force pushing pulse causes less recoil of the catheter at the flexible portion than where the acoustic radiation force pushing pulse is at the maximum amplitude over the first duration but without the modulation. A processor is operable to detect tissue motion in response to the acoustic radiation force pushing pulse. The tissue motion has a greater magnitude than a magnitude of the recoil. A display is operable to output tissue response as a function of the tissue motion.

In a second aspect, a method is provided for reduction of motion artifacts in ultrasound imaging. A flexible transducer transmits acoustic radiation force into the tissue of a patient. Displacement of the tissue in response to the acoustic radiation force is measured. An ultrasound image is generated as a function of the displacement. The acoustic radiation force is shaped in amplitude, time, or amplitude and time such that the acoustic radiation force has an envelope other than a rectangular envelope.

In a third aspect, a non-transitory computer readable storage medium has stored therein data representing instructions executable by a programmed processor for reduction of motion artifacts in ultrasound imaging. The storage medium includes instructions for obtaining ultrasound data representing a first region of a patient, generating a waveform configured to displace tissue by 2-8 micrometers, measuring the displacement of the tissue in the first region in response to the waveform, the measuring being with ultrasound scanning of the first region after the generating of the waveform and with comparing to the obtained ultrasound data, and stabilizing a transducer, the transducer movable in response to transmission of the waveform, into a linear movement region with a shape of the waveform, the waveform being less than 10 milliseconds.

In a fourth aspect, a non-transitory computer readable storage medium has stored therein data representing instructions executable by a programmed processor for reduction of motion artifacts in ultrasound imaging. The memory can store one or several pulses configured to set a dynamic response of the transducer. The acoustic pulse sequences represent a modulation of duration and amplitude of acoustic pulses, the modulation having variation in the amplitude, duration, or amplitude and duration, the variation configured to set the transducer response in a given operating environment.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
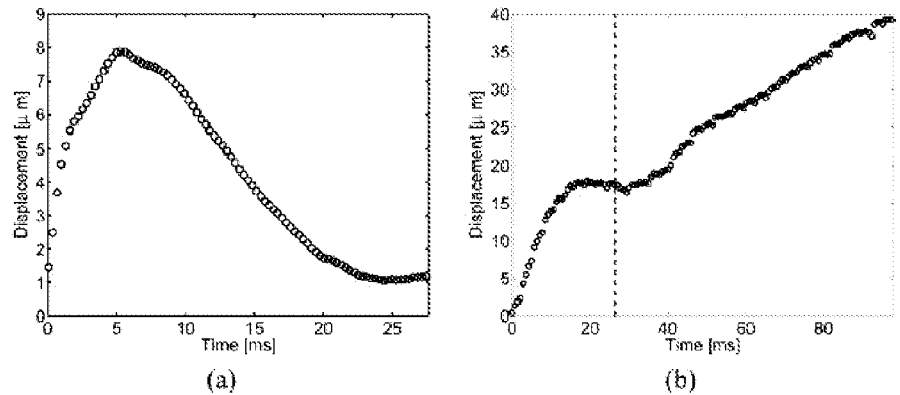
FIG. 1a is graph showing displacement of a catheter in response to transmission of acoustic radiation force.
FIG. 1b is a graph showing displacement of a catheter in response to a sequence of acoustic radiation force transmissions.

Acoustic transmissions may cause a moveable transducer, such as a flexible catheter, to recoil or bounce. The recoil may lead to improper alignment or spatial assignment for the returned echoes. The recoil may have a particular adverse effect for acoustic radiation force impulse (ARFI) imaging. ARFI pushing pulses applied to a focused area induces a shear and/or longitudinal wave. In response, tissue's displacement increases and then recovers, resulting in a temporal displacement profile. The displacement is measured. Recoil may cause the displacement measurement to be inaccurate.

The motion artifacts due to transmission from flexible or moveable ultrasound transducers may be reduced or minimized. To reduce the motion artifact, the acoustic pulses are optimally designed so that the pulses achieve a desired dynamic response, or displacement profile, from the transducer. The shaping is optimized in time and/or amplitude, such as varying the amplitude in ARFI pushing pulses. For example, the ARFI pushing pulses are designed to achieve the desired transducer displacement profile, whether stationary or linear.

The optimal pulse or pulse sequence may be based on a model of the dynamics of the transducer. The optimal pulse is one that achieves both the required level of acoustic insonification to support the imaging mode (ARFI) while achieving a desired dynamic response from the transducer (e.g. minimal motion). The methods for achieving this optimal pulse may be implemented using control theory and the control of flexible structures. For example, the inputs to the transducer as a flexible structure are recorded along with the dynamic response of the transducer as captured by sensors. Sensors might include the image data (raw or processed) received by the transducer, or other sensors, such as accelerometers or position sensors. A dynamic model may then be fitted to the recorded inputs and outputs. For example, a $1^{st}$ or $2^{nd}$ order dynamic model describing the impulse response of the motion of the moveable transducer may be estimated or determined through the methods of experimentation, modeling and system identification of flexible structures.

A dynamic model describing the transfer function of the acoustic force acting on the flexible structure of the transducer to the displacement, velocity and acceleration of the transducer, in the appropriate operating environment (blood pool of a heart chamber, for example) exists. The dynamic model is used to design an optimal acoustic pulse that achieves both adequate radiation force for pushing and a desired dynamic response. The dynamic model can be generated through experimentation or through system identification where the inputs to the transducer as a flexible structure are recorded along with the dynamic response of the transducer as captured by sensors.

One or several pulses are configured to achieve a dynamic response of the transducer (e.g. minimal displacement). The optimal acoustic pulse sequences represent a modulation of number, duration and amplitude of acoustic pulses that are designed to achieve the desired transducer response in one or several operating environments. That is, there could be one acoustic pulse sequence for operating in the left atrium of the heart and one for operating in the left ventrical. Each of these operating environments involves a different arrangement of the transducer acting in a more or less known configuration. The configuration can be characterized in a manner that constrains a dynamic model.

In an alternative, one or multiple completely defined dynamic model(s) that define the dynamic response of the transducer to acoustic pulses in one or several operating conditions are provided. A processor may then calculate the optimal acoustic pulse that achieves the desired transducer response and adequate acoustic radiation force using the appropriate stored dynamic model.

In another alternative, the dynamic model is calculated based on measurements taken during the operation of the transducer in the actual operating environment. Calculating the dynamic model involves using the methods of system identification, for example generating a parametric or non-parametric model of the dynamic model of the transducer based on observing the transfer of known acoustic input signals to measured sensor output signals. The sensors can include position sensors, accelerometers and/or the received acoustic signals and image. The appropriate dynamic model for the current configuration is created. The model is then used to determine the optimal pulse for that configuration.

Figure 2:
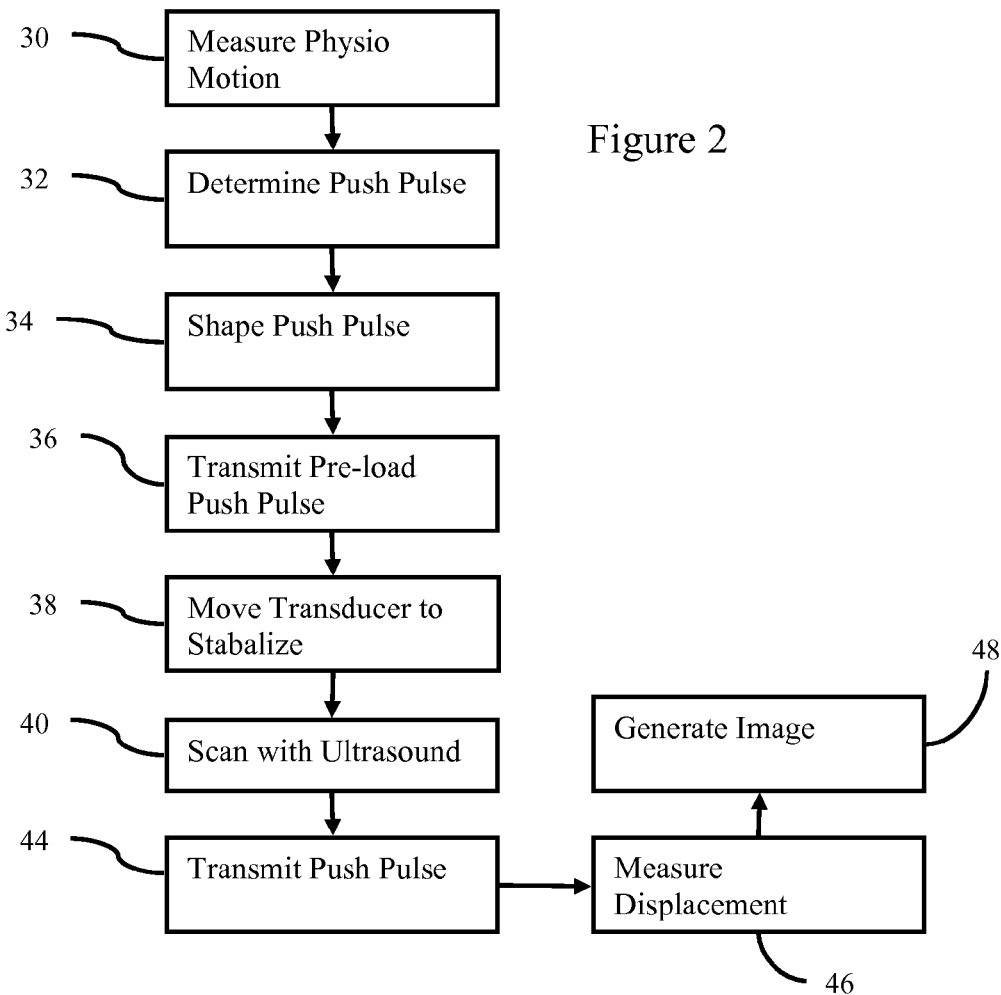
FIG. 2 is a flow chart of one embodiment of a method for reduction of motion artifacts in ultrasound imaging.

FIG. 2 shows a method for reduction of motion artifacts in ultrasound imaging. The method is implemented by the system of FIG. 8 or a different system. Additional, different, or fewer acts may be provided. For example, acts 30, 32, and/or 36 are not performed. As another example, acts 34, 40, 44, 46, and 48 are performed alone or in any combination. The acts are performed in the order described or shown, but may be performed in other orders. For example, act 38 is performed in conjunction with or as part of act 44.

In one embodiment, the process operates with an assumed model and creates a one size fits all optimal pulse. The model is assumed for a given environment based on experimentation. There may be more than one assumed model to account for different operating conditions. An optimal ARFI pulse is selected, designed, or used that minimizes the recoil motion for an assumed model and operating condition/environment. The optimal ARFI push pulse is fired. Optionally, the results are fed back to adjust the ARFI pulse to further minimize motion. An image is then created with the transducer in the desired response mode. In another embodiment, the model is identified in real-time on the system. The model is identified based on input or output data, such as received ultrasound data or data from sensors on the transducer. The model is used to determine an optimal ARFI pulse that minimizes the recoil motion for the operating condition and/or environment. The optimal ARFI push pulse is transmitted. Optionally, the motion of the transducer is monitored, and this information is fed back to adjust the identified model or identification of the model to use. An image is then created with the transducer in the desired response mode.

FIG. 2 shows example implementations of the above described concepts. The pulses are designed to control motion of the transducer in a given operating environment.

Acts 30 and 32 are performed for real-time modeling or optimization of the transmit pulses. As an alternative, the transmit pulses are preprogrammed based on assumptions. In yet another alternative, acts 30 and 32 are performed in design to preprogram one or more transmit pulses for later use.

Figure 3:
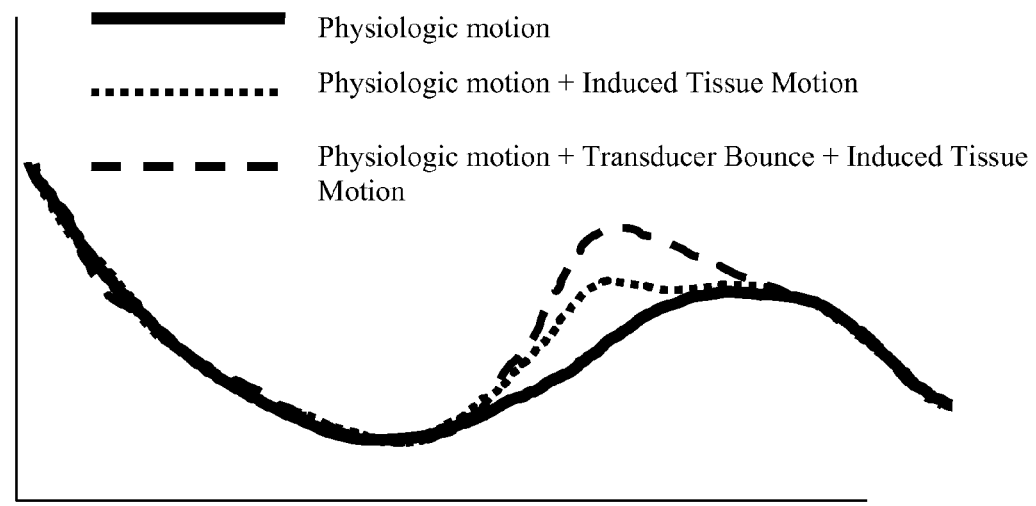
FIG. 3 is an example graph of motion at a focal region.

To determine a desired pulse shape, the motion characteristic of the transducer is determined. The motion observed during use includes three components: 1) physiologic motion, 2) ARFI induced tissue motion, 3) transducer "bounce" motion. FIG. 3 shows a representation of the three components of motion as a function of time. The separation of the three components begins at the transmission of the ARFI pulse. For other portions, the ARFI pushing pulse has attenuated or has not yet been transmitted, leaving just the physiological motion.

To arrive at an estimate of the transducer "bounce" motion, the physiologic and ARFI induced tissue motion are extracted or separated. Extracting the ARFI induced tissue motion may be achieved by sending tracking or interrogation pulses at times and/or locations that are separate from the ARFI push pulse. For example, a region spaced away in time or location from the focal location or beam of the ARFI push pulse is scanned. The difference between motion at the other regions or times as compared to the focal or beam region indicates the ARFI induced motion. To see what motion looks like without the influence of the ARFI induced tissue motion, data is acquired from places or times away from the push pulse.

The other component of motion is the physiological motion. Heart or breathing motion has a repeating pattern, but the pattern may be irregular. In act 30, an amount of motion due to physiological movement of the tissue is measured. The measurement is complicated by irregularity, such as associated with electrophysiology (EP) examination. In EP examination, the heart rhythms are not expected to be periodic.

To measure the physiologic motion, the region of interest, such as focal or beam region for the ARFI transmission or a larger scan region is scanned repetitively over several cycles, but without ARFI pushing pulse transmission. Alternatively, the motion is measured at other locations.

The motion may be modeled, and the model may be fit to the scan data or underlying motion. For example, a recursive model or Kalman filter are used to determine the tissue displacement as a function of time, such as represented in FIG. 3. The tissue displacement is measured for one location or for multiple locations.

As an alternative, the tissue motion may be assumed. For example, the tissue motion curve of FIG. 3 is used regardless of the patient.

Once the physiological model is determined, the amount of motion at any time may be estimated from the model. A region may be scanned, such as by the interrogation pulses of act 40 or other scans. The position of the tissue and/or a change between sequential scans may be used to determine the time relative to the physiological model. The motion at the time at which the ARFI pushing pulses is to be transmitted is extrapolated or determined from the model.

The tissue displacement is subtracted from measured displacement to determine motion of the transducer in response to the ARFI pushing pulse. The motion of the transducer is to be separated from the displacement of the tissue caused by the ARFI.

The motion of the transducer is determined by accounting for tissue motion. The tissue motion is measured with low amplitude pulses associated with less transducer recoil. The tissue motion is measured again in response to an ARFI push pulse. By subtracting out the physiological motion, the combination of pushing pulse displacement and transducer motion is determined. To separate these two motions, the motion of the transducer may be modeled and/or motion indicated at different locations or times is used.

In another embodiment, a scan (e.g., interrogating a region with B-mode pulses) is initiated from different portions of the array. The relative arrival time of echoes from a known location may be compared. Assuming that the transducer array is relatively rigid as compared to the flexible transducer, the deviation of time of return may be converted into distance. Using the time and distance information, the motion of the transducer may be determined without the subtracting out the physiologic motion.

As an alternative or in addition, the ARFI pushing pulses may be gated to the physiological cycle. The model indicates the amount of tissue motion for the selected gate time. The model may also indicate the amount of motion for other scans, such as scans in act 46 to measure displacement.

In one embodiment, the motion of the transducer is determined without measuring physiological motion. A sensor on the transducer may be used. For example, an accelerometer, position sensor and/or other inertial sensors indicate the amount and vector direction for transducer motion.

Instead of or in addition to separate sensors, the transducer 56 may be used to measure the motion of the transducer 54. Scans of regions spaced from the beam or focal region of the ARFI are performed. The regions are where displacement from the ARFI is low. The tissue motion is tracked over time. The physiologic motion determined without the ARFI transmission is subtracted from the tissue motion, providing the transducer motion.

Figure 4:
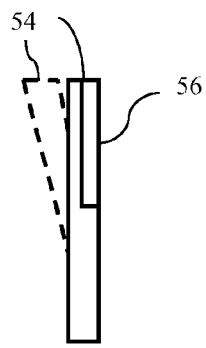
FIG. 4 is a side view of an example flexible transducer bending in response to acoustic transmission.

FIG. 4 shows example displacement of the transducer 56 on a catheter 54. The catheter 54 is shown as straight in solid lines. In response to transmission of one or more acoustic pulses, the catheter 54 flexes, as represented by the dashed lines. The relative amount of flex may be more or less. The transducer 56 may be rigid or flexible. The transducer 56 moves with the movement of the catheter. By positioning one or more sensors on the catheter 54 and/or the transducer 56, the motion may be determined.

The various scans are performed at the same time or times within the physiological cycle. Alternatively, modeling is used to interpolate or extrapolate the motion at a same time from measurements made at different times during the cycle.

In act 32, the pulse is determined. The pulse is used as a continuous waveform and/or a waveform for a given scan purpose. For example, the pushing pulse may be tens or hundreds of cycles. During each cycle, the pulse has a zero value for three instants (i.e., transitions through zero). As another example, a pulse includes one or more micro or millisecond periods of zero due to amplitude or temporal modulation. No other transmissions occur during the periods. The separate parts of the pulse are part of an overall pulse. Any type of pulse may be used, such as for B-mode or flow mode. In one embodiment, higher power or amplitude pulses are used, such as for ARFI. Separate pulses may be transmitted, such as where a longer period of time (e.g., 1 millisecond) separates the waveforms (pulses).

In one embodiment, the pulse is determined in act 32 based on assumptions. The recoil response is estimated, predicted, or measured in typical or other situations. The pulse is designed based on the assumption that actual use is similar. For example, a catheter is assumed to contact a vessel or heart wall about 4 cm from a tip of the catheter. Assuming standard flexibility and placement, most usage is similar. A pulse designed for the particular type of catheter, likely positioning, and likely ARFI settings is preprogrammed and used without further input. During actual use, the physiological motion and transducer motion are not measured. Instead, the transducer motion profile is assumed.

In another embodiment, the pulse is determined in act 32 by selection. One or more parameters during use indicate one of two or more possible pulses to use. For example, the user inputs or scanning indicates a position of a catheter, such as at what distance from the tip the catheter is in contact with tissue or a guide. As another example, the transducer motion is measured. The direction of motion, amount of motion, twist, strain, bending location, or other characteristic of motion of the transducer is measured. One of a plurality of possible pulses is selected based on the measured motion. The transducer motion may be from a sensor. The transducer motion may be determined without accounting for physiological movement of the tissue, such as by using a sensor. Alternatively, the desired pulse is selected by determining transducer motion by subtracting out physiological motion of the tissue.

In yet another embodiment, the pulse is determined in act 32 using modeling, such as a dynamic real-time determination. The pulse is determined as a function of a model matched to the flexible transducer while within the patient. The pulse is selected or designed as a function of a flex characteristic of the transducer while within the patient. The pulse is determined by selecting from a plurality of possible pulses or is determined by shaping based on the model. One or more characteristics of the model are related by a function or look-up table to one or more characteristics of the pulse. The characteristic of the fitted model determines the settings for the pulse.

The structural dynamics of the transducer may be determined through a sensor arrangement that gives displacement, velocity or acceleration as a function of time. This inertial information is used to generate a dynamic model of the transducer's structural dynamics as the transducer is being used. Other measures of the transducer's structural dynamics may be used, such as based on transducer motion determined from ultrasound data or amounts of bending based on strain gauges. An estimated or assumed structural dynamics may be used in other embodiments.

Ultrasound data may be used to determine the dynamics. Scanning (e.g., interrogation pulses) is used without a dynamic model to measure motion due to the ARFI push pulse. The scan is of regions away from the push pulse focus or beam. The transducer component of this motion is derived and removed. The remaining physiologic motion may be used in a model, such as to generate or tune the model. Alternatively, the ultrasound data is used to determine the transducer motion. The transducer motion is used to tune or configure the model.

With knowledge of the transducer's structural dynamics, the model is used to create an optimal pushing pulse or pulse sequence for the transducer. Any model may be used, such as a first or second order structural model. For example, a second order structural model includes inertia and damping information.

The determination of the pulse in act 32 provides a shaped pulse in act 34. One or more pulses are shaped. The shape controls the transducer motion to behave in a desired way. The desired manner may be to minimize transducer or other displacement after a final pushing pulse and before a series of tracking pulses. The desired motion may be to position the transducer into a linear displacement portion of the movement profile. For example, the shaping may allow control over the transducer motion to position the movement for further transmissions into the linear region represented after 30 ms in FIG. 1b, but without as long of transition or lead in time (e.g., provide linear movement in response to the first shaped push pulse or after only 5-10 ms of push pulses).

Any shaping may be used. The pulse is modulated in amplitude, time (duration), or amplitude and time. For amplitude modulation, any envelope shape may be provided, such as a linear ramp up to a maximum amplitude with a sudden off, a sudden on to a maximum amplitude with a more gradual decline in amplitude, a Gaussian envelope, stepped envelope with one or more cycles occurring at each amplitude in the stepped envelope, other non-linear envelope and/or combinations thereof. Any amplitude modulation of the transmit pulse having a desired effect on the motion of the transducer for the given or subsequent transmissions may be used. The amplitude modulation may have periods of zero amplitude within the pulse. The waveform includes a gap having no acoustic transmission, a non-linear envelope over a majority of the acoustic radiation force, or combinations thereof. Additionally or alternatively to amplitude variation within the pulse, the amplitude may vary between pulses in sequence.

For temporal modulation, pulse width, frequency, or other temporal changes in the pulse may be used. For example, a plurality of zero or lower amplitude time periods may be provided at a regular or irregular interval and for regular or irregular lengths. The periods of zero amplitude may correspond to fewer than one or more cycles. The temporal modulation may provide variation of durations within a pulse and/or variation of durations between pulses.

The variation in the pulse and/or sequence may keep the flexible transducer in a stable position (i.e., little or no movement). The variation may move the flexible transducer to a stable position for subsequent transmissions. The variation may move the flexible transducer into a range of positions associated with more predictable movement, such as linear movement.

Figure 5:
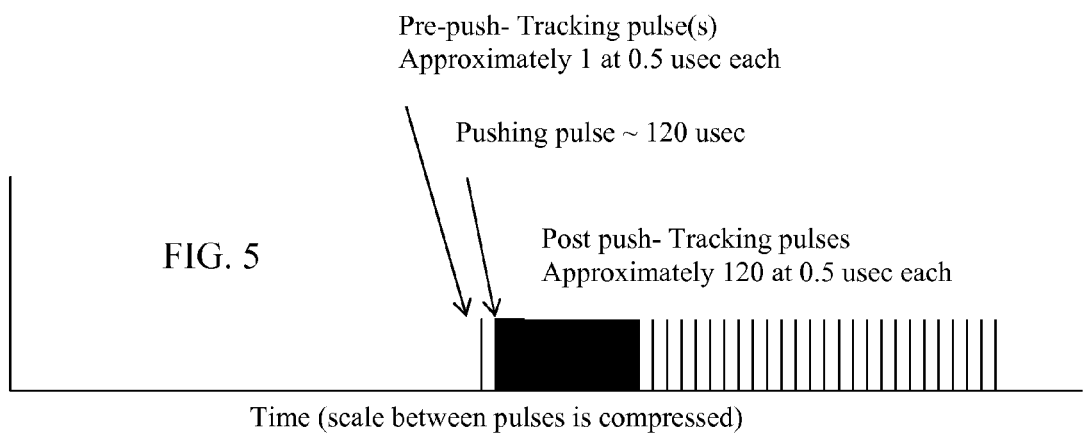
FIG. 5 is a graphic representation of an acoustic radiation force imaging transmission sequence.

FIG. 5 shows an example ARFI sequence. A first scan is performed to represent the tissue in a steady state. The ARFI pushing pulse is transmitted, such as an approximately 100-

200 microsecond pulse. The pushing pulse is followed by a plurality of tracking pulses, such as B-mode scans in the beam or focal region of the pushing pulse. The entire sequence is repeated for different regions. The force of the ARFI pushing pulse may cause the transducer to move during the tracking, distorting the displacement determination.

Figure 6:
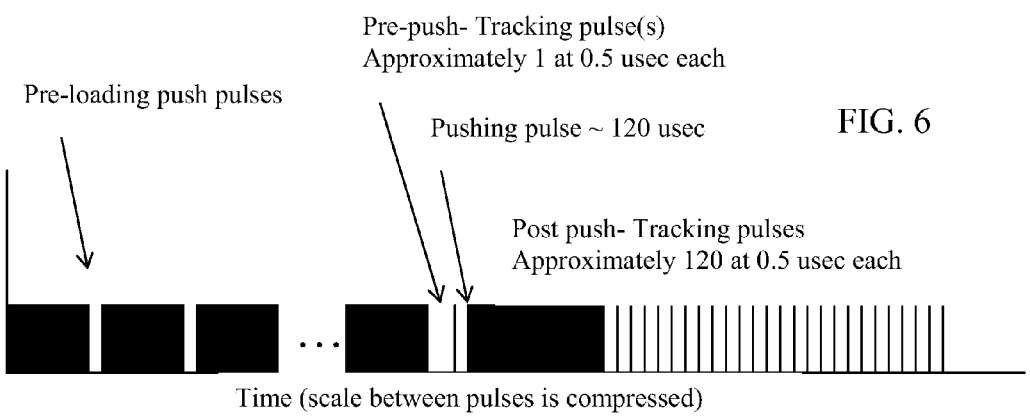
FIG. 6 is a graphic representation of an acoustic radiation force imaging transmission sequence with pre-loading.

FIG. 6 shows the approach of FIG. 5, but with initial or preliminary pushing pulses. The long duration (e.g., 100-200 microsecond) pushing pulses are repeated for about 20-30 ms to position the transducer in a region of linear motion for then performing the sequence shown in FIG. 5. The repetition of the sequence of FIG. 5 keeps the transducer in the linear motion region. FIG. 1b shows the movement profile for the sequence of FIG. 6. The transducer is moved to a linear motion region through brute force or repetition of the pushing pulse rather than shaping of the pushing pulse.

Figure 7:
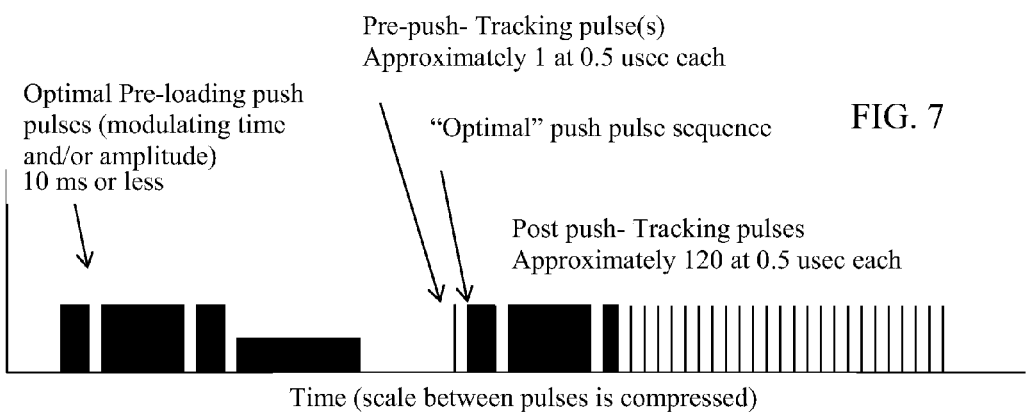
FIG. 7 is a graphic representation of an acoustic radiation force imaging transmission sequence with amplitude and temporal modulation.

FIG. 7 represents the use of shaping instead. The preliminary or initial pulse or pulses are shaped relative to each other and/or are themselves shaped to position the transducer to recoil (or not) in a desired way in response to pushing pulses during displacement measurement. The pushing pulse during displacement measurement is also shaped. Non-shaped or pulses with a rectangular envelope may be used for the initial or preliminary pulses or for the pushing pulse for displacement measurement. In one embodiment, the preliminary pulses are not used. The shaping of the ARFI imaging pushing pulse alone is sufficient to control the motion of the transducer. To the extent there is a sequence of pushing pulses, the sequence may be shaped with or without shaping the individual pulses to position the transducer at the desired portion of the motion profile during ARFI imaging. FIG. 7 is only one example of a pulse sequence being used to either pre-load the transducer or to optimally deliver acoustic pushes that achieve the desired displacement profile of the transducer.

In act 36, any preliminary or initial pulses are transmitted. The preliminary pulses predispose the transducer to a given position or to a location within the movement profile. By using shaping, the transducer more likely may be positioned as desired in less than 10 milliseconds. One or more preliminary pulses in a sequence are transmitted, such as the initial (e.g., preload) pulses shown in FIG. 7 with temporal or amplitude modulation in one pulse and amplitude modulation in the sequence of two pulses. The transmission occurs before the ARFI imaging to predispose the transducer into a linear movement region or a region likely to provide more stability during the ARFI imaging.

In act 38, the flexible transducer moves due to recoil from the initial pushing pulse. The transducer is flexible by being mounted on a moveable probe, such as a catheter, intravascular, transesophegeal, or other housing with flexibility. The probe is moveable by allowing bending, rotation, twisting, or translation. The transducer array may be rigid or flexible. For example, the array has a hinge or is bendable such that different portions of the array itself may move by different amounts due to recoil. The mount of the array may be flexible, allowing the entire array to move in response to recoil, whether the array is flexible or not.

The flexible transducer moves due to transmitting acoustic energy. For pulses with greater power due to larger aperture, greater amplitude, longer duration, or other characteristic, more recoil force may be provided. The recoil may or may not occur for pulses with lower power, such as B-mode or Doppler pulses transmitted within the FDA limits in on-going imaging. ARFI pushing pulses or other pulses may have temporarily greater power than B-mode or Doppler pulses, so may cause more recoil force. Depending on the flexibility or other constraints on motion, the transducer may not move in response to lower power pulses but move in response to higher power pulses. The transducer may move due to any power of pulses, but the movement for lower power pulses may be insignificant relative to the spatial resolution. Other transducers may cause misalignment even for lower power transmissions.

The shaping alters the amount of movement caused by the pulse. For example, one or more of the initial ARFI pushing pulses transmitted in act 36 cause the transducer to move more or less due to the shaping than without shaping (e.g., transmitting a pushing pulse with a rectangular envelope). The initial pushing pulses are an effort to predispose the transducer for imaging. Alternatively, the shaping causes the flexible transducer to not move due to recoil from the initial pushing pulses. The transmissions for scanning to determine displacement do not use shaping in addition to any shaping provided for imaging, but may include shaping to control transducer movement.

The transmission of the ARFI pushing pulse in act 44 may also move the transducer. Alternatively, the initial pushing pulses move the transducer to a location of more steady state stability given the amount of recoil and timing expected for each repetition of act 44. The transmissions of act 44 then do not move the transducer, at least to an amount causing large motion artifact, due to shaping. In another alternative, the initial pushing pulses of act 36 move the transducer to a portion of the movement profile associated with more linear or other desired motion. The transmissions of act 44 move the transducer, such as in a linear manner. The linear motion may result in an acceptable motion artifact or a motion artifact more easily removed from the displacement measurements. Acceptable motion artifact may correspond to reducing recoil to less than half of an average tissue displacement caused by the transmitting at a focal region. Even greater reduction of the motion artifact may be provided, such as reduction to 10% or less of the maximum or average tissue displacement caused by the transmission.

The energy (amplitude and/or duration) shaping of the initial pushing pulses is the same or different than the energy shaping of the ARFI pushing pulses. For example, an ARFI pushing pulse has a maximum amplitude within 50% of the maximum amplitude of any of the initial pushing pulses. Maximum amplitudes within 40%, 20%, or the same may be provided. The maximum amplitudes may be more than 50% different. The amplitudes may be different due to the different purposes. The initial pushing pulses are to predispose the transducer to a desired position or inertia. The ARFI pushing pulses are shaped to maintain regular motion or to result in reduced, little or no motion due to recoil. The shaping may also be used to counteract other sources or motion.

By shaping, the transducer may be stabilized into a desired movement region (e.g., linear movement region) with a waveform or sequence of waveforms lasting less than 10 milliseconds. More than 10 milliseconds, less than 5 milliseconds or other amount of time may be used for the initial pushing pulse sequence. Lesser amounts of time result in less overall power being applied to the patient, making it more likely not to exceed FDA limits on heating. The linear movement region may correspond to ongoing movement or no movement.

By shaping the ARFI in amplitude, time, or both using modulation of the waveform, the transducer may be stabilized. For example, the ARFI pushing pulse has an amplitude envelope that is other than rectangular shaped. The waveform has a duration less than 200 microseconds. The duration may be longer or shorter than with a rectangular envelope pushing pulse. By modulating the acoustic radiation force, the flexible transducer is stabilized in a first position or in a linear movement.

In act 40, a sequence of pulses is transmitted to tissue prior to application of a stress (i.e., ARFI pushing pulse). Ultrasound data representing a region, of the patient is obtained by scanning with ultrasound. The region is a point, line, area, or volume. The sequence forms beams at different locations to scan the region in any format. The transmission occurs before the ARFI pushing pulse of act 44 and measurement of the tissue response to the displacement in act 46. Since the tissue response to the stress may be measured before, after or both relative to the peak stress, the transmission for reference tissue position is performed prior to application of the stress and after tissue has recovered from any preceding pushing pulses.

The ultrasound data obtained in response to the transmissions is used as tissue position reference information. The reference information is used to represent the tissue without the displacement for comparison to the displaced tissue. The scanning of act 40 may be gated to the cardiac cycle to remove or reduce the effect of physiological motion on the measurements of act 46.

To obtain the ultrasound data from the scan, electrical signals generated by the transducer in response to echoes from the transmission are received. The beamformed samples are detected. Any type of detection may be used, such as a B-mode detection of the intensity. The detected information is responsive to the transmitting prior to application of the stress.

In act 44, acoustic radiation force is transmitted from a flexible transducer. The ARFI is transmitted to tissue of a patient. The focal point is positioned within the region scanned in act 40. The ARFI pushing pulse, even with the shaping, has an amplitude, duration, and/or power configured to displace tissue by 2-8 micrometers on average. Greater or lesser power may be provided. The power is applied to the tissue. For example, acoustic radiation force focused at the region of interest or a point is transmitted.

When the ARFI pushing pulse is applied to a focused area, a longitudinal and/or shear wave is induced and propagates away from this focused area. A substantially single pressure wave is generated. The wave stresses the tissue. The tissue responds to the stress by moving. Relative to an original location, tissue is displaced. This displacement increases and then recovers to zero, resulting in a temporal displacement profile. The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest.

In act 46, the displacement of the tissue is measured. The tissue movement in response to the acoustic radiation force may be measured. The longitudinal or shear displacement may be measured. The displacement is measured at a point, along a line, at different locations in an area, or at different locations in a volume.

Act 46 occurs while the tissue is being subjected to and/or recovers from the stress. For example, ultrasound scanning (i.e., transmission and reception) occurs after application of the stress and before the tissue reaches a relaxed state.

The response of tissue along transmit or receive beams is detected. Doppler or B-mode scanning may be used: Ultrasound imaging is performed before, during and/or after the stress is applied. Ultrasound data is received in response to transmissions of ultrasound. A sequence of transmissions and receptions are provided for each spatial location within the region of tissue subjected to the stress.

Tissue motion is detected from the received ultrasound information of the scan. Motion responsive to a shear or longitudinal wave may be detected. The tissue motion is detected at different times. The different times correspond to different transmit events or repletion of the scanning. Alternatively, the tissue motion is detected at just one time.

Tissue motion is detected by estimating displacement relative to the reference tissue information. For example, the displacement of tissue along scan lines is determined by comparison of the data obtained in act 40 with data obtained in act 46. The displacement may be measured from tissue data, such as B-mode ultrasound data, but flow (e.g., velocity) information may be used. Coherent data or undetected data may be used, such as using beamformed data prior to detection.

Correlation, cross-correlation, minimum sum of absolute differences or other similarity measure is used to determine the displacement between scans. For example, each IQ data pair is correlated to the corresponding reference to obtain the displacement. Data representing a plurality of spatial locations is correlated with the reference data. The displacements are determined along one, two, or three dimensions.

The monitoring is performed for any number of scan lines. For example, four receive beams are formed in response to each transmission. After transmitting the acoustic force to generate the shear or longitudinal wave, B-mode transmissions are performed repetitively along a single scan line and receptions along four adjacent scan lines. Some of the ultrasound data, such as at the beginning or end of the repetitions, may not be responsive to the shear or other wave. In other embodiments, only a single receive beam or other numbers of receive beams are formed in response to each transmission. Each repetition monitors a same region or locations for determining tissue response for those locations.

The detection of tissue motion occurs while or after the echoes are received. In one embodiment, the received information is stored and may be used for later detection. In other embodiments, the received information is used for detection as the data is received.

Displacement velocity may be estimated. As the wave propagates through the scan lines, the B-mode intensity may vary. For the monitored scan lines, a sequence of data is provided representing a time profile of tissue motion resulting from the shear or longitudinal wave. For example, data from a plurality of spatial locations (e.g., along the scan lines) is correlated as a function of time. Any elasticity detection may be used. For each depth or spatial location, a correlation over a plurality of depths or spatial locations (e.g., kernel of 64 depths with the center depth being the point for which the profile is calculated) is performed. The spatial offset with the highest or sufficient correlation at a given time indicates the amount of displacement. For each location, the displacement as a function of time is determined. Two or three-dimensional displacement in space may be used. One-dimensional displacement along a direction different from the scan lines or beams may be used.

The tissue response, such as the peak displacement, may be used as a result. Alternatively, further calculations are performed, such as determining a time to displacement, displacement velocity, or a tissue mechanical property, such as strain, strain rate, elasticity, viscosity, impedance, or others.

Shear velocity is obtained by determining a time from generation of the shear wave until detection of the shear wave at a different location. The time and distance to the location determine the velocity. The distance is known from the scan line spacing (i.e., the transmit beam position for generating the shear wave and the receive beam position for detecting the shear wave). The time is known from the relative time between generation and detection of the shear wave. The peak indicates the shear wave.

As another example, a feature is extracted from the temporal profiles. Principal component decomposition may be used. A correlation between the different temporal profiles is performed. The lag associated with the different distances for the different temporal profiles provides the velocity. Alternatively, a wavelet analysis may be performed. A wavelet transform is applied to the temporal profiles to identify a peak or other characteristic corresponding to the shear wave. A velocity value is identified from the travel time of the peak to each spatial location.

Acts 40, 44 and 46 may repeated, with or without repetition of acts 36 and 38. The repetition is for different regions. The repetitions include use of shaped pulses to stabilize or keep the transducer stabilized. The shaped pulses are the same or different for different repetitions.

In act 48, an image may be generated. The image is generated as a function of the displacement, such as modulating a display characteristic as a function of the tissue response. For example, elasticity information is displayed. Shear information may be displayed. For example, the shear velocity is displayed. The displacement information may be displayed on the image or without the image. A representation of displacement may be used instead of an actual number, such as mapping a color or otherwise modulating the pixels at the region of interest as a function of the displacement information. For example, a high displacement is mapped to a brighter red than a lower displacement.

The displacement information may be indicated relative to a range of values with or without other displacement information. For example, a bar, line, graph or other representation of a range of shear velocities, elasticities, or strains is displayed. The range may be for tissue or may be specific to type of tissue. For example, the user inputs or a processor identifies the type of tissue for which displacement is measured. A range of normal and abnormal displacements for that type of tissue is output. The range does or does not indicate normal or abnormal. The estimated displacement information is shown on the range, such as an arrow or other indicator. The relative position may be more intuitive to a user.

The displacement may be used to generate the image. For example, the image pixels are modulated by the peak displacement. As another example, the image pixels are modulated by the time to the peak displacement. Such an image may indicate regions or locations associated with different (e.g., slower or faster) response to the stress. Any tissue response imaging may be used, such as strain, strain rate, elasticity, shear wave or other now known or later developed imaging.

Figure 8:
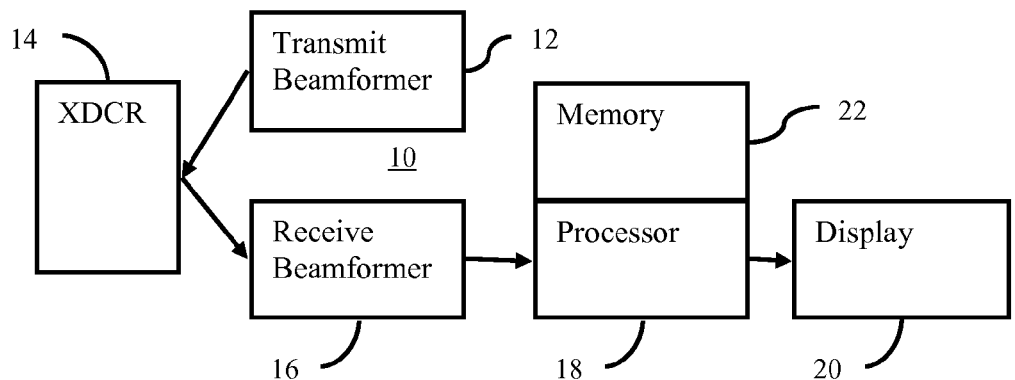
FIG. 8 is a block diagram of one embodiment of a system for reduction of motion artifacts in ultrasound imaging.

FIG. 8 shows one embodiment of a system 10 for reduction of motion artifacts in ultrasound imaging. The system 10 implements the method of FIG. 2 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, tissue properties to be determined, region of interest selection, selection of transmit sequences, pulse shape parameters, or other control. The system 10 is a medical diagnostic ultrasound imaging system. In alternative embodiments, the system 10 is a personal computer, workstation, PACS station, or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. The transmit beamformer 12 generates and causes transmission of ARFI, B-mode, Doppler, or other pulses.

Upon transmission of acoustic waves from the transducer 14 in response to the generated waves, one or more beams are formed. A sequence of transmit beams are generated to scan a two or three-dimensional region. Sector, Vector®, linear, or other scan formats may be used. The same region is scanned multiple times. For flow or Doppler imaging and for strain imaging, a sequence of scans is used. In Doppler imaging and shear velocity estimation, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The transmit beams are formed at different energy or amplitude levels. Amplifiers for each channel and/or aperture size control the amplitude of the transmitted beam. Transmit beams to generate a shear wave, longitudinal wave, and/or for strain imaging may have greater amplitudes than for imaging or monitoring for the displacement.

The transmit beamformer 12 generates an acoustic radiation force pushing pulse and/or initial pushing pulses. Each of the pushing pulses has a maximum amplitude and lasts for a given duration. The duration may be of any length, such as less than 200 microseconds, less than 150 microseconds or between 100-200 microseconds.

To control transducer bounce or recoil, one or more of the acoustic radiation force pushing pulses are modulated in amplitude. The amplitude varies during the pulse or waveform. The pulse with amplitude modulation includes an envelope that varies. The envelope may have a shape other than rectangular or Gaussian, such as having a ramped, stepped, or other shape. The variation may or may not include one or more zero amplitude periods.

A sequence of pulses, such as preliminary pushing pulses, separated by periods of no acoustic transmission may be transmitted. A sequence of at least one pre-loading pushing pulse may be generated prior to the generation of the acoustic radiation force pushing pulse. The sequence has a duration less than 10 microseconds, such as transmitting one, two, three, or fewer than ten pulses of 100-200 microseconds. Other numbers of pulses and/or length of each pulse may be used. The preliminary pulses are shaped to control motion of the transducer. The shaping may be modulation in amplitude or a constant amplitude without modulation (e.g., rectangular envelope). The pre-loading pushing pulses have a shape to position the ultrasound transducer in a stable position or a position of linear motion due to recoil from the sequence.

By shaping the ARFI pushing pulse and/or the pre-loading pulses, the transducer recoils less. For example, the acoustic radiation force pushing pulse causes less recoil of the catheter at the flexible portion than where the acoustic radiation force pushing pulse is at the same maximum amplitude over the same duration but without the modulation. The shaping results in less recoil than using a waveform without shaping. The variation in amplitude, time, or both stabilizes the ultrasound transducer in a position or in a linear movement as compared to no variation in amplitude and/or time.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The transducer 14 is moveable or flexible. For example, the transducer 14 includes a rigid array supported in a housing that bends, twists, rotates, and/or translates. For example, the transducer 14 is a catheter, such as an intracardiac catheter (e.g., the AcuNav™ catheter from Siemens Medical Solutions USA, Inc.). Other flexible transducers 14 include IVUS, TEE, hinged, balloon mounted, or other transducers.

The transmit beamformer 12 and receive beamformer 16 connect with the same elements of the transducer 14 through a transmit/receive switch or multiplexer. The elements are shared for both transmit and receive events. One or more elements may not be shared, such as where the transmit and receive apertures are different (only overlap or use entirely different elements).

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to a transmission. In alternative embodiments, the receive beamformer 16 is a processor for generating samples using Fourier or other transforms.

The receive beamformer 16 may include a filter, such as a filter for isolating information at desired frequency bands. A band pass filter, or demodulator and band or low pass filter may be used. For rapid detection, parallel paths may be provided for receive beamforming separately for different beams. Alternatively, a processor operating pursuant to software performs the filtering, beamforming, or combinations thereof.

The receive beamformer 16 outputs beam summed data representing spatial locations at a given time. Data for a single location, locations along a line, locations for an area, or locations for a volume are output. Dynamic focusing may be provided. The data may be for different purposes. For example, different scans are performed for B-mode or tissue data than for elasticity, shear, or strain estimation. Data received for B-mode or other imaging may be used for estimation of displacement.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, network, server, group of processors, data path, combinations thereof or other now known or later developed device for detecting and processing information for display from beamformed ultrasound samples. In one embodiment, the processor 18 includes one or more detectors and a separate processor. The processor 18 performs any combination of one or more of the acts shown in FIG. 2.

The processor 18 detects tissue motion in response to the acoustic radiation force pushing pulse. Due to the shaping of the pushing pulse and/or pre-loading pulses, the tissue motion has a greater magnitude than a magnitude of the recoil. The displacement of tissue is more than 50% larger than displacement due to transducer motion. For example, the shear or longitudinal motion has a maximum or average of 2 to 10 microns displacement, and the recoil is less than 1 micron. Other maximums, averages, and relative differences may be provided.

The processor 18 detects the tissue motion as displacement. The displacement is detected from an ultrasound scan prior to or after the generation of the acoustic radiation force pushing pulse and another ultrasound scan after the generation of the acoustic radiation force pushing pulse and during tissue recovery. Tissue motion over a range of times may be detected. The tissue motion responsive to a shear or longitudinal wave is calculated. The peak displacement, magnitude of displacement at a given time, displacement profile, shear wave velocity or other information is estimated. Linear regression, correlation, principal component extraction, wavelet transforms, cubic spline interpolation, or other estimation techniques may be used.

Where real-time feedback from ultrasound data is used to shape the ARFI pushing pulse and/or preliminary pushes, the processor 18 measures an amount of motion due to physiological movement of tissue. The selection of the shaping and resulting waveform is a function of transducer motion and the motion due to physiological movement of the tissue. The shaping, including the maximum amplitude and the duration, is determined as a function of a second order structural model matched to the catheter while within the patient.

Alternatively, the processor 18, in response to user input or other measurements, selects the acoustic radiation force pushing pulse from a plurality of possible pulses. In yet other embodiments, the pulse is preprogrammed and not processor selection is used.

The processor 18 generates display data, such as graphic overlays and images. The display data is in any format, such as values before mapping, gray scale or color-mapped values, red-green-blue (RGB) values, scan format data, display or Cartesian coordinate format data, or other data. The processor 18 outputs data appropriate for the display device 20.

The processor 18 operates pursuant to instructions stored in the memory 22 or another memory. The processor 18 is programmed for reduction of motion artifacts in ultrasound imaging. The memory 22 is a computer readable storage media. The instructions for implementing the processes, methods and/or techniques discussed herein are provided on the non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display device 20 is a CRT, LCD, projector, plasma, printer, or other display for displaying shear velocity, graphics, user interface, validation indication, two-dimensional images, or three-dimensional representations. The display device 20 displays ultrasound images, the displacement information (e.g., shear, shear velocity, strain, elasticity or others), and/or other information. For example, the display 20 outputs tissue response information. The displayed information is in a report or screen presentation and is a function of the tissue motion. An image representing the tissue response to the shear or longitudinal wave may be output.

The display device 20 is operable to output a range associated with a type of tissue and indicate the estimated displacement information within the range. The display device 20 receives the graphics information for from the processor 18. The display device 20 generates a visual representation of the graphic, such as the bar or other range scale. An indication of the estimated displacement information relative to the range is also generated, such as generating an arrow, color, bar, text, or other graphic adjacent to, overlaid on, combined with, or associated with the range.

The display device 20 outputs an image of a region of the patient, such as a two-dimensional elasticity, Doppler tissue, or B-mode image. The image includes a location indicator for the displacement information, such as the shear velocity.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system for reduction of motion artifacts in ultrasound imaging, the system comprising:
   a catheter comprising an ultrasound transducer and a flexible portion;
   a first processor configured to determine an acoustic force radiation pushing pulse to be transmitted by a transmit beamformer;
   the transmit beamformer configured to generate the acoustic force radiation pushing pulse determined by the first processor, the acoustic force radiation pulse having a maximum amplitude and lasting for a first duration, the acoustic force radiation pushing pulse being modulated in amplitude, the modulation comprising variation such that transmission of the acoustic force radiation pushing pulse causes less recoil of the catheter at the flexible portion than where the acoustic force radiation pushing pulse is at the maximum amplitude over the first duration but without the modulation, the variation of the modulation being a function of the recoil of the catheter;
   an image processor configured to detect tissue motion in response to the acoustic force radiation pushing pulse, the tissue motion having a greater magnitude than a magnitude of the recoil; and
   a display operable to output tissue response as a function of the tissue motion.

2. The system of claim 1 wherein the first duration is less than 200 microseconds, the image processor configured to detect the tissue motion from a first ultrasound scan prior to the generation of the acoustic force radiation pushing pulse and a second ultrasound scan after the generation of the acoustic force radiation pushing pulse.

3. The system of claim 1 wherein the variation comprises distinct waveforms separated by at least one period of no acoustic transmission.

4. The system of claim 1 wherein the variation comprises a waveform having an envelope shape other than rectangular.

5. The system of claim 1 wherein the variation stabilizes the ultrasound transducer in a first position or in a linear movement.

6. The system of claim 1 wherein the image processor is configured to detect the tissue motion as shear or longitudinal motion of tissue in the tissue region, the shear or longitudinal motion at a maximum being 2 to 10 microns and the recoil being less than 1 micron.

7. The system of claim 1 wherein the transmit beamformer is configured to generate a sequence of pre-loading pushing pulses prior to the generation of the acoustic force radiation pushing pulse, the entire sequence having a second duration less than 10 milliseconds, the pre-loading pushing pulses having a shape operable to position the ultrasound transducer in a stable position or a position of linear motion due to recoil from the sequence.

8. The system of claim 1 wherein the image processor is configured to measure an amount of motion due to physiological movement of tissue, the motion due to physiological movement of the tissue different than the motion of the tissue detected in response to the acoustic force radiation pushing pulse, and configured to select the acoustic force radiation pushing pulse from a plurality of possible pulses, the selection being a function of transducer motion and the motion due to physiological movement of the tissue.

9. The system of claim 1 wherein the first processor is further configured to determine the maximum amplitude and the first duration as a function of a second order structural model matched to the catheter while within the patient.

* * * * *